United States Patent [19]

Hobo et al.

[11] 4,445,855
[45] May 1, 1984

[54] ARTICULATION DETECTOR CRT FOR ARTICULATORS

[75] Inventors: Sumiya Hobo, Tokyo; Koji Okamoto, Suita, both of Japan

[73] Assignee: Shioda Dental Manufacturing Co., Ltd., Tochigi, Japan

[21] Appl. No.: 415,460

[22] Filed: Sep. 7, 1982

[30] Foreign Application Priority Data

Sep. 9, 1981 [JP] Japan .................. 56-143070

[51] Int. Cl.³ .................................. A61C 11/00
[52] U.S. Cl. ........................... 433/59; 433/27; 433/56
[58] Field of Search .............. 433/56, 55, 27, 32, 433/59, 68, 69, 57; 33/174 D; 324/415

[56] References Cited

U.S. PATENT DOCUMENTS

| | | | |
|---|---|---|---|
| 2,205,775 | 6/1940 | Henez | 433/68 |
| 2,543,512 | 2/1951 | Shapiro | 433/68 |
| 2,605,378 | 7/1952 | Carpenter | 324/415 |
| 3,350,782 | 11/1967 | Guichet | 433/56 |
| 3,382,581 | 5/1968 | Balazs | 433/27 |

*Primary Examiner*—John J. Wilson
*Attorney, Agent, or Firm*—Stevens, Davis, Miller & Mosher

[57] ABSTRACT

An articulation detector for articulators of the kind wherein condylar elements mounted on a lower jaw member and glenoid fossae assemblies of an upper jaw member are made of a conductive material, comprises an electric power source, a luminous element and a pair of detecting electrode, all of which are connected in series. The electrodes are adapted to be connected to the lower jaw member and an incisal pin mounted on the upper jaw member of the articulator when the detector is in use. The adjustment of the articulator or prosthetic appliances may be detected by observing the light emitted from the luminous element.

2 Claims, 10 Drawing Figures

ARTICULATION DETECTOR CRT FOR ARTICULATORS

This invention relates to an articulation detector and its use. More particularly, it relates to an articulation detector for adjustments of articulators or prosthetic appliances and a method for adjusting an articulator with checkbites to reproduce jaw movements of a patient on the articulator.

When fabricating prosthetic appliances such as dental prosthesis or crowns in the toothed or edentulous jaw, there are prepared maxillary and mandibular casts by using impressions of a patient, and also eccentric checkbites, i.e., left and right and protrusive interocclusal records, are taken of the patient's mouth. The maxillary and mandibular casts are mounted on an articulator by the known face-bow transfer in centric relation. The articulator with the casts is transferred to a dental laboratory together with the face-bow record and the checkbites and, then, the condylar adjustments of the articulator are made by using the eccentric checkbites to simulate the angulation between the occlusal plane of the teeth and the functional plane of the glenoid fossae. The articulator thus adjusted simulates the jaw movements, so that the dental technician may make a prosthetic appliance with these maxillary and mandibular casts mounted on the articulator.

The condylar adjustments of the articulator have conventionally been made by fitting the casts into the checkbites and moving dials or thumbnuts while observing the glenoid fossae until the condylar elements are in contact with the walls of the housings. Since the checkbites are made of wax, they may be deformed or invalidated by a slight force applied thereto during the condylar adjustments, thus making it difficult to accomplish accurate condylar adjustments. Also, when fabricating crowns, the final occlusal adjustments have been made by fitting the crown to be completed into the maxillary or mandibular casts mounted on the articulator, and then detecting the force required for pulling out a thin paper placed between the incisal pin and the incisal guide. Thus, it is very troublesome to accomplish the final occlusion adjustments.

It is therefore an object of the present invention to provide an articulation detector for adjustments of articulator or prosthetic appliances that makes it possible to accomplish quick and accurate adjustments of articulators or prosthetic appliances.

Another object of the present invention is to provide a method for adjusting an articulator that makes it possible to accomplish quick and accurate condylar adjustments of the articulator.

According to the present invention there is provided an articulation detector for articulators of the kind wherein condylar elements mounted on a lower jaw member and glenoid fossae assemblies of an upper jaw member are made of a conductive material, comprising an electric power source, a luminous element, and a pair of detecting electrodes, all of which are connected in series, said electrodes being adapted to be connected respectively to the lower jaw member and an incisal pin mounted on the upper jaw member of the articulator when the detector is in use.

The invention will be described in more detail with reference to the accompanying drawings which are by way of example only and thus are not limitative of the present invention, and wherein.

Figure 8:
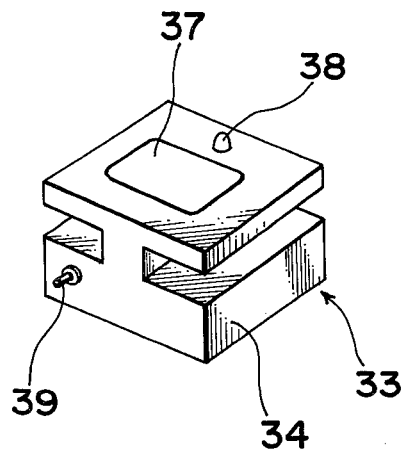
FIG. 8 is a perspective view of an articulation detector according to the present invention.
Figure 9:
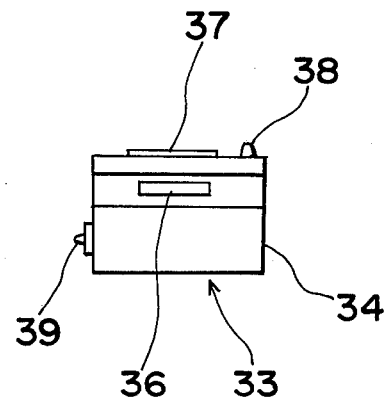
FIG. 9 is a side view of the detector shown in FIG. 8.
Figure 10:
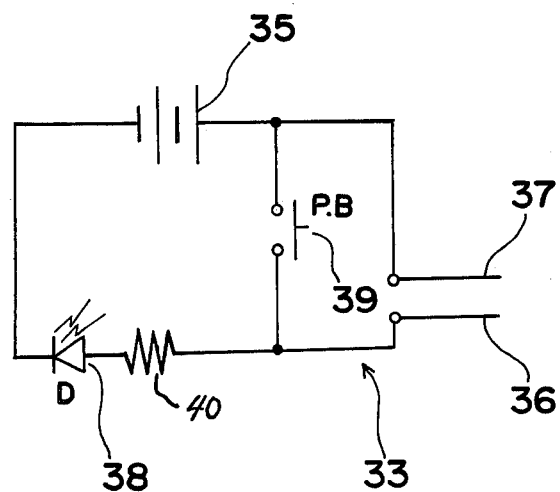
FIG. 10 is a circuit diagram of the detector shown in FIG. 8.

Referring to FIGS. 8 to 10, there is shown an articulation detector 33 which comprises a power source 35 such as a battery or a cell, a pair of detecting electrodes 36 and 37, a luminous element such as a miniature lamp or light-emitting diode 38, and a resistor 40, all of which are connected in series. Numeral 39 is a testing switch for checking the power source 35. The power source 35 and light-emitting diode 38 are housed in a body 34 so that the light from the light-emitting diode 38 can be observed from the outside. The body 34 has been made of an insulating material such as synthetic resin and formed into the same shape that an incisal guide of the articulator has. The body may have any shape different from that of the incisal guide. In this case, one of the electrodes is connected to the condylar shaft, and the other may be mounted on the top of the incisal guide. The electrodes 36 and 37 have been arranged so that they may be respectively connected to the lower jaw member 2 and the incisal pin 7 when the detector 33 is mounted on the anterior part of the lower jaw member of the articulator instead of the incisal guide. The light-emitting diode 38 is lighted when the upper and lower jaw members are in position as mentioned below.

Referring now to FIGS. 1 to 7, there is shown an arcon type semi-adjustable articulator 1 for carrying out one embodiment of the present invention. The articulator 1 comprises a lower jaw member 2 and an upper jaw member 6, on which mandibular and maxillary casts may be secured by means of thumbnuts 23 and 24, respectively. The lower jaw member 2 is provided with a spaced pair of condylar supports 3 extending upwardly from its posterior laterals. A pair of condylar shafts, on each of which a sphere-shaped condylar element 4 is fixed, are mounted in the free ends of the supports 3 by a spring clip and screw mechanism and, they extend therefrom in the horizontal and inward directions on the same axle. On the anterior part of the lower jaw member 2 there is an articulation detector 33 instead of an incisal guide, on which an incisal pin 7 may rest. The incisal pin 7 is replaceably mounted in the anterior part of the upper jaw member 6 by a thumbnut 25.

The upper jaw member 6 comprises a base 8 and glenoid fossae assemblies rotatably mounted on posterior laterals of the base 8. The fossae assembly comprises an arm 11 rotatably mounted on posterior laterals of the base 8. Pivotally mounted on the arms 11 are centric latches 9 adapted to hold the condylar elements 4 within the glenoid fossae at centric permitting the upper and lower jaw members 6 and 2 to be opened and closed, yet return to the same position each time. Laterally slidable housing members 14 have been fixed on the arm 11 by a locknut 17, and the medial wall members 19 have been fixed on the housing member 14 by a locknut. The medial wall members may move along an arcuate guiding track of the housing member 14 when the locknut is loosened. Each housing member may move along a groove 13 placed in the arm 11.

The superior wall 15 and posterior wall 16 of the housing member 14, medial wall 20 of the medial wall member 13 and the anterior wall of the centric latch 9 form a condylar guidance, similar to the anatomy of the glenoid fossae as found in the skull.

According to the present invention, the condylar adjustments of the articulator thus constructed may be carried out in the following manner.

Figure 1:
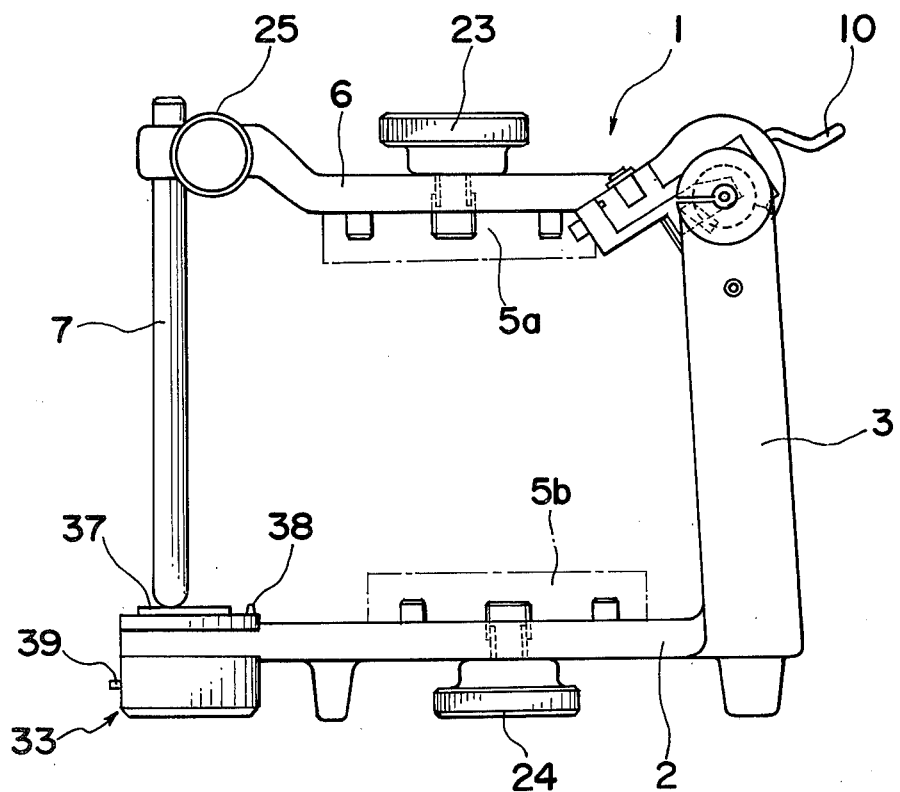
FIG. 1 is a side view of an articulator for carrying out one embodiment of the present invention.
Figure 2:
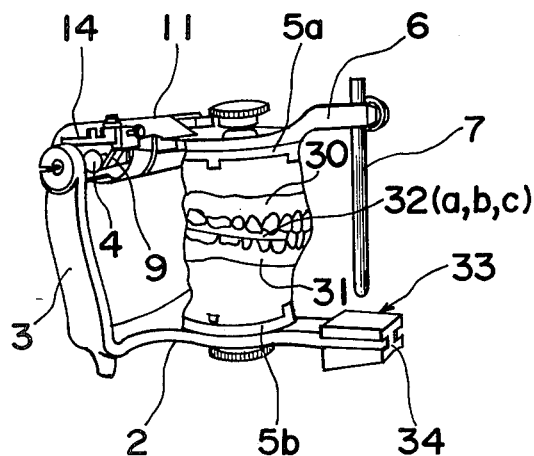
FIG. 2 is a perspective view of the articulator shown in FIG. 1 with maxillary and mandibular casts mounted thereon.
Figure 3:
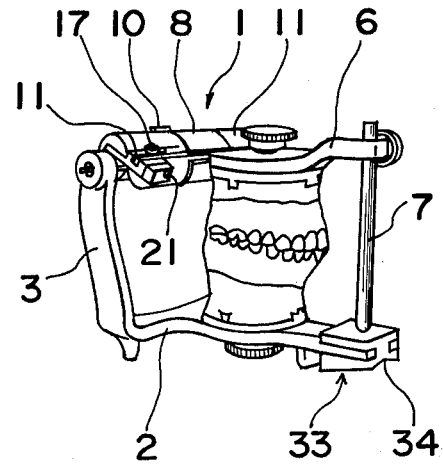
FIG. 3 is a perspective view of the articular shown in FIG. 1 with the articulator adjusted.
Figure 4:
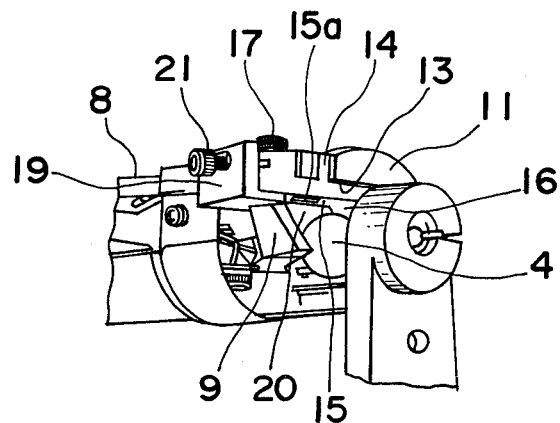
FIG. 4 is an enlarged fragmentary view of the articulator in the status shown in FIG. 2.
Figure 5:
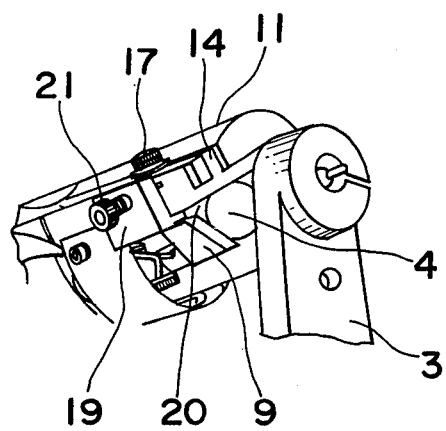
FIG. 5 is an enlarged fragmentary view of the articulator in the status shown in FIG. 3.
Figure 7:
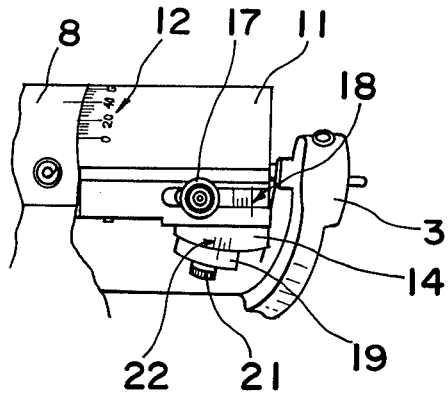
FIG. 7 is an enlarged fragmentary plan view of the articulator in the status shown in FIG. 2.
Figure 6:
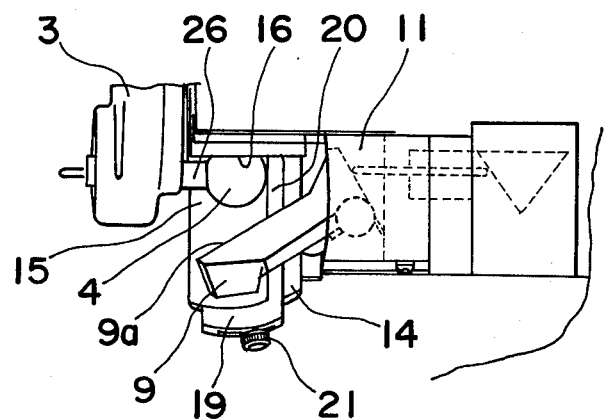
FIG. 6 is an enlarged fragmentary bottom view of the articulator with a centric latch released.

The detector 33 is mounted on the anterior part of the lower jaw member 2 as shown in FIGS. 1 to 3, and the maxillary and mandibular casts 30 and 31 are respectively mounted on mounting rings 5a and 5b by the known face-bow transfer with the centric interocclusal record. The mounting rings 5a and 5b have been secured to the upper and lower jaw members 6 and 2 by thumbnuts 23 and 24. In addition, the centric latches 9 are released by turning the release lever 10 so that the articulator may take any eccentric position. The incisal pin has been set free by loosening the thumbnuts. The arms 11 are set in horizontal position, or, the inclination of sagittal condyle path is set at 0 degrees. The medial wall members 19 have been slid to the innermost positions. After such arrangements have been accomplished, the straightforward protrusive checkbit 32a is placed between the maxillary and mandibular casts to set the articulator in the protrusive position where the superior and posterior walls 15 and 16 of the housing 14 are detached from the superior surface of the condylar elements 4. The light-emitting diode 38 is therefore not lighted, although the incisal pin 7 is in contact with the electrodes 37d.

In order to reproduce the lowermost position of the temporomandibular joints, where the lower jaw is protruted forwardly, on the articulator, one of the arms 11 of the articulator is turned on its axis until the superior wall 15 of the housing 14 is lightly brought into contact with the condylar element 4. Since the light-emitting diode 38 is lighted when the wall 15 is brought into contact with the condylar element 4, the contact can be detected by the light emitted from the light-emitting diode 38. Thus, an accurate inclination of the sagittal protrusive condyle path can be determined by reading the calibrations 12 on the arm 11.

The immediate side shift of the articulator may be adjusted by using left and right lateral checkbites in the following manner. In this case, centric latch has been released and the incisal pin 7 has been rested on the detector 33. One of the lateral checkbits, for example, the right lateral checkbite is mounted between the maxillary and mandibular casts after removing the protrusive checkbite. When fitting the casts into the right lateral checkbite, the upper jaw member will be turned about the right condylar element 4. The left arm 11 is then turned on its axis so that the superior wall 15 of the housing 14 is brought into contact with the condylar element 4. The contact between them can be also detected by the light emitted from the light-emitting diode 38. The position at which the light-emitting diode is lighted is calibrated as inclinations of the sagittal lateral condylar path. After the calibration, the arm 11 is returned in position, and the inner wall member 19 is slid laterally along the guiding track of the housing 14 until the light-emitting diode 38 is lighted. The position of the inner wall member 19 at which the diode is lighted is calibrated as an amount of the immediate side shift. Similar procedures are made with the left lateral checkbite to calibrate the inclination of the sagittal left lateral condyle path and the left immediate side shift. These are done to reproduce the lateral movements of the lower jaw of the patient on the articulator. During the condylar adjustments in relation to one of the glenoid fossae, the other condylar element should be insulated from the condylar assembly by using a suitable insulating material such as an insulating paper.

Accurate reproduction of the jaw movements on the articulator makes adequate occlusal analysis possible by observing the resulting changes. This makes it possible to fabricate an adequate dental prosthesis for the patient. If the mounting records are retained throughout the course of treatment, and the mounting is identified with the articulator used, it may be placed back onto the same articulator whenever it is required.

According to the present invention, the adequate positions of the members of the articulator can be detected electrically, thus making it possible to reproduce the movements of the eccentric jaw relationship accurately on the articulator without invalidation of the eccentric checkbites. Further, the adjustments can be accomplished with ease only by checking the lightening of the luminous element. In addition, when making the final occlusal adjustments of the prosthetic appliances, it is possible with the light emitted from the luminous element to detect whether the adjustment of the prosthetic appliance has been completed, without use of thin papers.

What is claimed is:

1. An articulation detector for adjustments of an arcon type semi-adjustable articulator, comprising a body having the same shape as an incisal guide of the articulator and having means for mounting on an anterior part of a lower jaw member of the articulator, a power source housed in the body, a luminous element so arranged in the body that the light emitted therefrom can be observed from the outside, and a pair of electrodes connected in series with said power source and said luminous element, one of said electrodes being mounted on the top of the body on which an incisal pin removably mounted in an upper jaw member of the articulator may rest, the other electrode being so arranged that it is connected with a lower jaw member of the articulator.

2. An arcon type semi-adjustable articulator comprising a lower jaw member having a spaced pair of condylar supports extending upwardly from its posterior laterals, an upper jaw member provided with adjustable glenoid fossae assemblies rotatably mounted on its base, a pair of condylar elements mounted on condylar shafts extending from free ends of said supports in the horizontal and inward directions on the same axis, said condylar elements being held in the glenoid fossae of said assemblies to permit the upper and lower jaw members to be opened and closed, yet return to the same position each time, an incisal pin removably mounted in the anterior part of the upper jaw member, and an articulation detector removably mounted on the anterior part of the jaw member, said articulation detector comprising a body adapted to serve as an incisal guide of the articulator, a power source housed in the body, a luminous element so arranged in the body that the light emitted therefrom can be observed from the outside, and a pair of electrodes connected in series with said power source and said luminous element, one of said electrodes being mounted on the top of the body on which said incisal pin may rest, the other electrode being so arranged that it is connected with the lower jaw member.

* * * * *